(12) United States Patent
Kirino et al.

(10) Patent No.: US 10,662,480 B2
(45) Date of Patent: May 26, 2020

(54) SPECIFIC EXPRESSION OF HALF-TRNA IN CANCERS

(71) Applicant: THOMAS JEFFERSON UNIVERSITY, Philadelphia, PA (US)

(72) Inventors: Yohei Kirino, Bryn Mawr, PA (US); Shozo Honda, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 392 days.

(21) Appl. No.: 15/116,452

(22) PCT Filed: Feb. 4, 2015

(86) PCT No.: PCT/US2015/014421
§ 371 (c)(1),
(2) Date: Aug. 3, 2016

(87) PCT Pub. No.: WO2015/120022
PCT Pub. Date: Aug. 13, 2015

(65) Prior Publication Data
US 2017/0314076 A1    Nov. 2, 2017

Related U.S. Application Data

(60) Provisional application No. 61/935,795, filed on Feb. 4, 2014.

(51) Int. Cl.
*C12Q 1/68* (2018.01)
*C12Q 1/6886* (2018.01)
*C12Q 1/6874* (2018.01)

(52) U.S. Cl.
CPC ......... *C12Q 1/6886* (2013.01); *C12Q 1/6874* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 5,585,089 A | 12/1996 | Queen et al. | |
| 2005/0089913 A1 * | 4/2005 | Williams | C12N 15/1034 506/1 |
| 2007/0020630 A1 | 1/2007 | Trotta | |

FOREIGN PATENT DOCUMENTS

| WO | 2000027340 A2 | 5/2000 |
| WO | 2012068383 A2 | 5/2012 |

OTHER PUBLICATIONS

Elbarbary, Reyad A., et al. "Modulation of gene expression by human cytosolic tRNase ZL through 5'-half-tRNA." PLoS one4.6 (2009): e5908. (Year: 2009).*
Elbarbary supp Fig. S4 (Year: 2009).*
Lee et al.(Genes & development 23.22 (2009): 2639-2649) (Year: 2009).*
Maroney et al.( Nature protocols 3.2 (2008): 279) (Year: 2008).*
Schnnittgen et al.( Methods 44.1 (2008): 31-38.) (Year: 2008).*
Lee 2009 supp (Year: 2009).*
Thompson et al. ( Rna 14.10 (2008): 2095-2103). (Year: 2008).*
Yamasaki, Satoshi, et al. "Angiogenin cleaves tRNA and promotes stress-induced translational repression." The Journal of cell biology 185.1 (2009): 35-42. (Year: 2009).*
"Comprehensive molecular portraits of human breast tumors", Nature, vol. 490, No. 7418, pp. 61-70, 2012.
Elbarbary, R.A., et al., "Modulation of Gene Expression by Human Cytosolic tRNase ZL through 5'-Half-tRNA", PLoS One, vol. 4, No. 6, pp. 1-12, 2009.
Emara, M.M., et al., Angiogenin-induced tRNA-derived stress-induced RNAs promote stress-induced stress granule assembly, J Biol Chem, vol. 285, No. 14, pp. 10959-10968, 2010.
Fu, H., et al., "Stress induces tRNA cleavage by angiogenin in mammalian cells", FEBS Lett, vol. 583, No. 2, pp. 437-442, 2009.
Goll, M.G., et al., "Methylation of tRNAAsp by the DNA methyltransferase homolog Dnmt2", Science, vol. 311, No. 5759, pp. 395-398, 2006.
Grzybowska-Szatkowska, L., et al., "Polymorphisms in genes encoding mt-tRNA in female breast cancer in Poland", Mitochondrial DNA, vol. 23, No. 2, pp. 106-111, 2012.
International Search Report issued in International Application No. PCT/US2015/014421 and dated May 27, 2015.
Ivanov, P., et al., "Angiogenin-induced tRNA fragments inhibit translation initiation", Molecular Cell, vol. 43, No. 4, pp. 613_623, 2011.
Kirino, Y., et al., "Codon-specific translational defect caused by a wobble modification deficiency in mutant tRNA from a human mitochondrial disease", Proc Natl Acad Sci U S A, vol. 101, No. 42, pp. 15070-15075, 2004.
Kirino, Y., et al., "Acquisition of the wobble modification in mitochondrial tRNALeu (CUN) bearing the G12300A mutation suppresses the MELAS molecular defect", Hum Mol Genet, vol. 15, No. 6, pp. 897-904, 2006.
Kirino, Y., et al., "Mouse Piwi-interacting RNAs are 2'-O-methylated at their 3' termini", Nat Struct Mol Biol, vol. 14, No. 4, pp. 347-348, 2007.
Köhler, G., et al., "Derivation of specific antibody-producing tissue culture and tumor lines by cell fusion", Eur. J. Immunol, vol. 6, No. 7, pp. 511-519, 1976.
Lee, Y.S., et al., "A novel class of small RNAs: tRNA-derived RNA fragments (tRFs)", Genes & Development, vol. 23, No. 22, pp. 2639-2649, 2009.

(Continued)

*Primary Examiner* — Tracy Vivlemore
*Assistant Examiner* — Sahana S Kaup
(74) *Attorney, Agent, or Firm* — Cozen O'Connor

(57) ABSTRACT

The present invention relates to systems, devices and methods for diagnosing cancer. In various embodiments, the present invention provides a method for quantifying a 5'-htRNA; a method for quantifying a 3'-htRNA; a method for obtaining a DNA library of 5'-htRNAs and a DNA library of 5'-htRNAs obtained therefrom; and a method for obtaining a DNA library of 3'-htRNAs and a DNA library of 3'-htRNAs obtained therefrom. The invention also teaches a method for determining the presence or absence of a cancer cell in a biological sample; a method of diagnosing cancer in a subject; and a method of prognosing cancer in a subject.

5 Claims, 10 Drawing Sheets

Specification includes a Sequence Listing.

(56) References Cited

OTHER PUBLICATIONS

Maute, R.L., et al., "tRNA-derived microRNA modulates proliferation and the DNA damage response and is down-regulated in B cell lymphoma", Proc Natl Acad Sci U S A, vol. 110, No. 4, pp. 1404-1409, 2013.
Riechmann, L., et al., "Reshaping human antibodies for therapy", Nature, vol. 332, No. 6162, pp. 323-327, 1988.
Schaefer, M., et al., "RNA methylation by Dnmt2 protects transfer RNAs against stress-induced cleavage", Genes & Development, vol. 24, No. 15, pp. 1590-1595, 2010.
Yamasaki, S., et al., "Angiogenin cleaves tRNA and promotes stress-induced translational repression", J Cell Biol, vol. 185, No. 1, pp. 35-42, 2009.

* cited by examiner

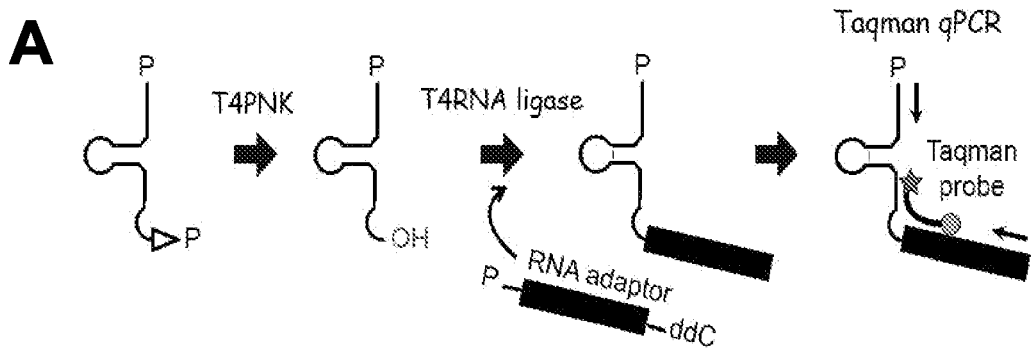
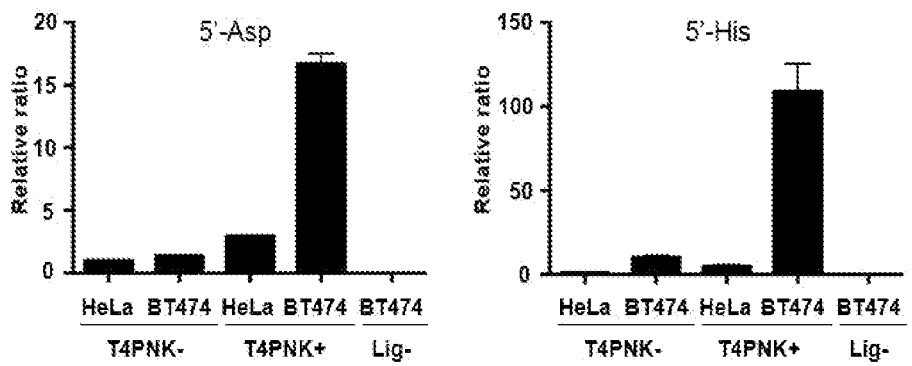
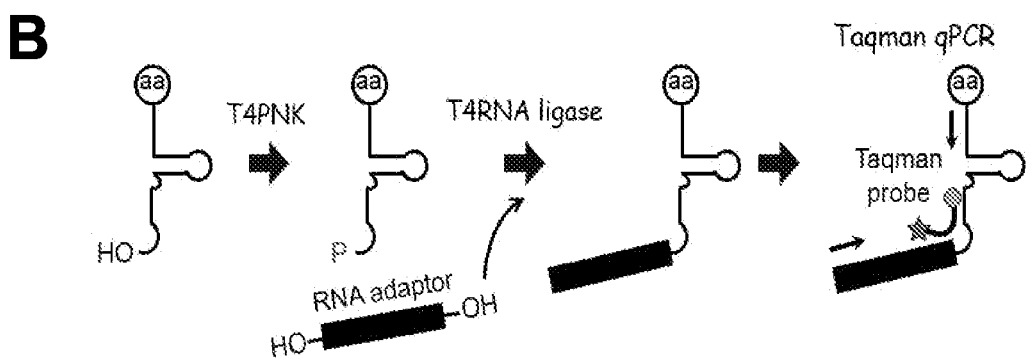
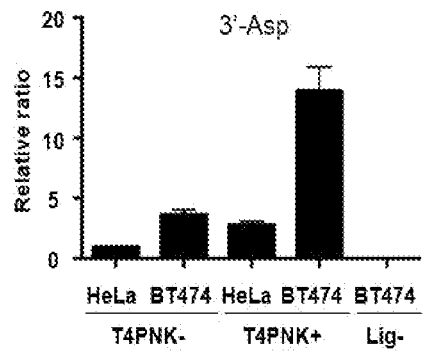
FIGs. 3A-3B

SPECIFIC EXPRESSION OF HALF-TRNA IN CANCERS

CROSS-REFERENCE TO RELATED APPLICATIONS

This application claims benefit under 35 U.S.C. § 119(e) of U.S. Provisional Application Ser. No. 61/935,795 filed on Feb. 4, 2014, the contents of which are herein incorporated by reference in its entirety.

FIELD OF INVENTION

The present invention generally relates to the field of medicine and cancer. More specifically, this invention relates to systems, devices and methods for diagnosing cancer.

BACKGROUND

All publications herein are incorporated by reference to the same extent as if each individual publication or patent application were specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

A non-coding RNA (ncRNA) is a functional RNA molecule that is not translated into a protein. Less-frequently used synonyms are non-protein-coding RNA (npcRNA), non-messenger RNA (nmRNA) and functional RNA (fRNA). The DNA sequence from which a non-coding RNA is transcribed is often called an RNA gene. Non-coding RNA genes include highly abundant and functionally important RNAs, such as transfer RNA (tRNA) and ribosomal RNA (rRNA), as well as RNAs such as snoRNAs, microRNAs, siRNAs, snRNAs, exRNAs, and piRNAs, and the long ncRNAs, such as Xist and HOTAIR. The number of ncRNAs encoded within the human genome is unknown, however recent transcriptomic and bioinformatic studies suggest the existence of thousands of ncRNAs.

During the last decade, significant attention has been directed towards the identification of novel small non-coding RNAs (sncRNAs). Recently, sncRNAs derived from tRNAs were identified as functional molecules, and not as by-products from random degradation (See Phizicky, E. M. and A. K. Hopper, tRNA biology charges to the front *Genes Dev,* 2010. 24(17): p. 1832-60; Sobala, A. and G. Hutvagner, Transfer RNA-derived fragments: origins, processing, and functions *Wiley Interdiscip Rev RNA,* 2011. 2(6): p. 853-62; Maute, R. L., et al., tRNA-derived microRNA modulates proliferation and the DNA damage response and is down-regulated in B cell lymphoma. *Proc Natl Acad Sci USA,* 2013. 110(4): p. 1404-9; and Lee, Y. S., et al. A novel class of small RNAs: tRNA-derived RNA fragments (tRFs). *Genes Dev,* 2009. 23(22): p. 2639-49, each of which is incorporated herein by reference in their entirety as though fully set forth).

There is a need in the art for diagnostic and therapeutic technologies based upon newly discovered ncRNAs and their respective functions.

SUMMARY

The following embodiments and aspects thereof are described and illustrated in conjunction with systems, compositions and methods which are meant to be exemplary and illustrative, not limiting in scope.

Various embodiments of the present invention provide a method for quantifying a 5'-htRNA in an RNA sample. In some embodiments, the method includes (a) treating the RNA sample with a polynucleotide kinase; (b) adding a 3'-RNA adaptor to the RNA sample; (c) treating the RNA sample with an RNA ligase; (d) adding an oligonucleotide probe targeting the boundary between the 5'-htRNA and the 3'-RNA adaptor to the RNA sample; (e) performing a quantitative RT-PCR (qRT-PCR) on the RNA sample; and (0 quantifying the 5'-htRNA in the RNA sample by detecting the qRT-PCR product. The present invention also teaches a nucleic acid generated according to this method.

In certain embodiments, the present invention provides a kit. In some embodiments, the kit includes a polynucleotide kinase; a 3'-RNA adaptor; an RNA ligase; an oligonucleotide probe targeting the boundary between a 5'-htRNA and the 3'-RNA adaptor; and instructions for using the kit to quantify the 5'-htRNA in a sample.

Various embodiments of the present invention provide a method for quantifying a 3'-htRNA in an RNA sample. In some embodiments, the method includes (a) treating the RNA sample with a polynucleotide kinase; (b) adding a 5'-RNA adaptor to the RNA sample; (c) treating the RNA sample with an RNA ligase; (d) adding an oligonucleotide probe targeting the boundary between the 5'-RNA adaptor and the 3'-htRNA to the RNA sample; (e) performing a quantitative RT-PCR (qRT-PCR) on the RNA sample; and (0 quantifying the 3'-htRNA in the RNA sample by detecting the qRT-PCR product. In some embodiments, the invention provides a nucleic acid generated according to this method.

In further embodiments, the present invention provides a kit. In some embodiments, the kit includes a polynucleotide kinase; a 5'-RNA adaptor; an RNA ligase; an oligonucleotide probe targeting the boundary between the 5'-RNA adaptor and a 3'-htRNA; and instructions for using the kit to quantify the 3'-htRNA in a sample.

Various embodiments of the present invention provide a method for obtaining a DNA library of 5'-htRNAs in an RNA sample. In some embodiments, the method includes (a) deacylating the RNA sample with a buffer having a pH value of at least 9.0; (b) treating the RNA sample with an alkaline phosphatase; (c) disrupting a 3'-OH end in the RNA sample with $NaIO_4$ oxidation; (d) treating the RNA sample with a polynucleotide kinase; (e) adding a 3'-RNA adaptor to the RNA sample; (f) treating the RNA sample with an RNA ligase; (g) adding a 5'-RNA adaptor to the RNA sample; (h) treating the RNA sample with an RNA ligase; and (i) performing a RT-PCR on the RNA sample, thereby obtaining the DNA library of 5'-htRNAs in the RNA sample. In some embodiments, the invention provides a DNA library of 5'-htRNAs obtained by this method.

Various embodiments of the present invention provide a method for obtaining a DNA library of 3'-htRNAs in an RNA sample. In some embodiments, the method includes (a) treating the RNA sample with a polynucleotide kinase; (b) disrupting 3'-OH ends in the RNA sample with $NaIO_4$ oxidation; (c) deacylating the RNA sample with a buffer having a pH value of at least 9.0; (d) adding a 3'-RNA adaptor to the RNA sample; (e) treating the RNA sample with an RNA ligase; (f) adding a 5'-RNA adaptor to the RNA sample; (g) treating the RNA sample with an RNA ligase; and (h) performing a RT-PCR on the RNA sample, thereby obtaining the DNA library of 3'-htRNAs in the RNA sample. In some embodiments, the invention provides a DNA library of 3'-htRNAs obtained by this method.

Various embodiments of the present invention provide a method for determining the presence or absence of a cancer cell in a biological sample. In some embodiments, the method includes (a) obtaining an RNA sample from the biological sample; (b) quantifying an htRNA in the RNA sample; and (c) determining the presence of a cancer cell in the biological sample if the quantified htRNA is more than a reference value of the htRNA quantity, or determining the absence of a cancer cell in the biological sample if the quantified htRNA is not more than a reference value of the htRNA quantity.

Various embodiments of the present invention provide a method of diagnosing cancer in a subject. In some embodiments, the invention includes (a) obtaining a biological sample from the subject; (b) obtaining an RNA sample from the biological sample; (c) quantifying an htRNA in the RNA sample; and (d) diagnosing that the subject has cancer if the quantified htRNA is more than a reference value of the htRNA quantity, or diagnosing that the subject does not have cancer if the quantified htRNA is not more than a reference value of the htRNA quantity.

Various embodiments of the present invention provide a method of prognosing cancer in a subject. In some embodiments, the invention includes (a) obtaining a biological sample from the subject; (b) obtaining an RNA sample from the biological sample; (c) quantifying an htRNA in the RNA sample; and (d) prognosing that the subject is likely to develop cancer if the quantified htRNA is more than a reference value of the htRNA quantity, or prognosing that the subject is not likely to develop cancer if the quantified htRNA is not more than a reference value of the htRNA quantity.

BRIEF DESCRIPTION OF THE DRAWINGS

Exemplary embodiments are illustrated in referenced figures. It is intended that the embodiments and figures disclosed herein are to be considered illustrative rather than restrictive.

FIGS. 3A-3B demonstrate, in accordance with an embodiment of the invention, an htRNA detection method.

(FIG. 5A) Using Northern blots for a tRNA'-derived piRNA, both htRNA$^{Asp}$ and piRNA were detected. The htRNA sequence shown on the right was confirmed by RACE. The arrow heads indicate the boarders of htRNA$^{Asp}$ and piRNA in the tRNA$^{Asp}$. (FIG. 5B) htRNA$^{Asp}$ expression was reduced in thymidine-treated cells whose proliferation was arrested, suggesting a correlation between htRNA expression and cell proliferation.

(FIG. 6A) Using Northern blots both 5'- and 3'-htRNA$^{Asp}$ were detected in MCF7 and BT474 breast cancer cells. (FIG. 6B) htRNA expression was specifically observed in breast cancer cells. (FIG. 6C) htRNA$^{Asp}$ and htRNA$^{His}$ sequences were determined by RACE. 3'-htRNA$^{His}$ was detected by Northern blot. The arrow heads indicate the border between 5'-htRNA$^{Asp}$ and 3'-htRNA$^{Asp}$ and the border between 5'-htRNA$^{His}$ and 3'-htRNA$^{His}$.

(FIG. 7A) The 5'-htRNA band detected using Northern blot was shifted up by phosphatase treatment (BAP removes P), and was even further shifted up by acid-treatment following the BAP reaction (HCl+BAP removes cyclic-P), indicating that 5'-htRNAs contain both phosphate (5'-end) and cyclic-phosphate (3'-end) at their termini. The presence of cyclic-phosphate was confirmed by the upward-shifted band by T4 Polynucleotide Kinase treatment (removes cyclic-P). miRNA-16 was used as a control. (FIG. 7B) NaIO$_4$ oxidation followed by β-elimination (NaIO$_4$, (3) removed the 3'-terminal nucleotides from 3'-htRNAs only after incubation with high pH buffer (deacylation), indicating the presence of amino acids at 3'-end of 3'-htRNA. There was no change with BAP, indicating the presence of a hydroxyl terminus at the 5'-end.

DETAILED DESCRIPTION

Figure 1:
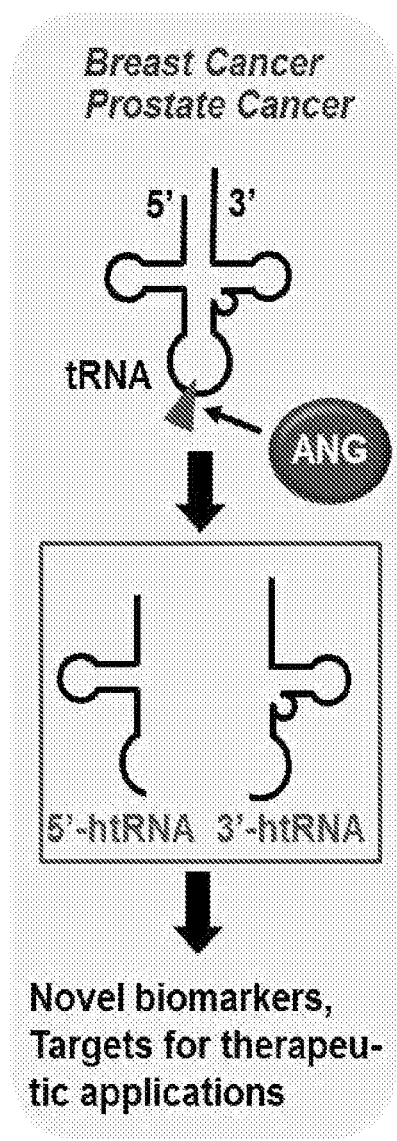
FIG. 1 demonstrates, in accordance with an embodiment of the invention, a schematic depiction of htRNAs and uses thereof.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry* Reactions, Mechanisms and Structure 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies *A Laboratory Manual* 2$^{nci}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For purposes of the present invention, certain terms are defined below.

"Tumor," as used herein refers to all neoplastic cell growth and proliferation, whether malignant or benign, and all pre-cancerous and cancerous cells and tissues.

"Cancer" and "cancerous" refer to or describe the physiological condition in mammals that is typically characterized by unregulated cell growth. Examples of cancer include, but are not limited to, B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

"Chemotherapy resistance" as used herein refers to partial or complete resistance to chemotherapeutic drugs. For example, when a subject does not respond or only partially responds to a chemotherapeutic drug. A person of skill in the art can determine whether a subject is exhibiting resistance to chemotherapy.

"Sequence identity" is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. By way of non-limiting example, sequence identity can be calculated by software such as BLAST-P, BLAST-N, or FASTA-N, or any other appropriate software that is known in the art. The substantially identical sequences of the present invention may be at least 80%, 85%, 90%, 95%, or 100% identical to sequences described herein.

"Treated" or "treatment" as used herein in the context of an assay means applying an effective amount of a substance under conditions that allow for the action of the substance. For example, "treating a sample with ligase" means applying a sufficient amount of ligase and under the appropriate conditions (buffers, temperature, etc.) to allow for ligation, as would be recognized by one of skill in the art.

Alkaline phosphatase (ALP, ALKP) (EC 3.1.3.1) is a hydrolase enzyme responsible for removing phosphate groups from many types of molecules, including nucleotides, proteins, and alkaloids. As the name suggests, alkaline phosphatases are most effective in an alkaline environment. It is sometimes used synonymously as basic phosphatase. Examples of alkaline phosphatase include, but are not limited to, bacterial alkaline phosphatase (BAP) and calf intestinal phosphatase (CIP).

By way of background, half-tRNAs (htRNAs) were discovered to be a novel class of tRNA-derived sncRNAs expressed in breast and prostate cancers at levels significantly higher than the relatively small levels at which they may be found in certain other cancerous and noncancerous cells. To date, htRNAs have neither been described nor systematically studied in cancer or other diseases, potentially due to their 3'-end structures. Although htRNAs have a similar biogenesis mechanism as that of tRNA-derived stress-induced RNAs (tiRNAs) (See Ivanov, P., et al., Angiogenin-induced tRNA fragments inhibit translation initiation. *Mol Cell*, 2011. 43(4): p. 613-23; Emara, M. M., et al., Angiogenin-induced tRNA-derived stress-induced RNAs promote stress-induced stress granule assembly. *J Biol Chem*, 2010. 285(14): p. 10959-68; Yamasaki, S., et al., Angiogenin cleaves tRNA and promotes stress-induced translational repression. *J Cell Biol*, 2009. 185(1): p. 35-42; and Fu, H., et al., Stress induces tRNA cleavage by angiogenin in mammalian cells. *FEBS Lett*, 2009. 583(2): p. 437-42), which are produced by ANG-mediated anticodon cleavage, several characteristics (e.g., tRNA source, expression patterns of both 5'- and 3'-halves, and association not with stress but with hormone receptors) indicate htRNAs to be novel sncRNAs.

5'-htRNAs and 3'-htRNAs contain cyclic phosphates and amino acids at their 3'-ends, respectively. Such 3'-end modifications would inhibit adapter ligation, a step in normal RNA-sequencing methods; consequently, htRNAs would not be detected by traditional RNA-sequencing. As htRNAs are not abundantly detected in the publicly available sequencing datasets in breast cancer cells, the discoveries presented herein shed light on hidden layers of sncRNA biology.

As demonstrated herein in various embodiments and reported experiments, a sensitive and convenient system of detecting htRNAs from a small quantity of RNA sample was established. This detection system could be widely used for htRNA expression analyses in various samples, including patient tissues. Therefore, htRNAs can be used as biomarkers for cancer patients. As demonstrated herein, htRNA expression in cancer cells was screened, revealing that htRNAs are expressed in relatively high levels in breast and prostate cancers, but not in the other tested cancer cells. Moreover, htRNA expression in breast cancer is associated with the estrogen receptor (ER) signaling pathway, suggesting that htRNAs are key factors in cancer pathogenesis. Because htRNAs are expressed in relatively high levels in breast and prostate cancers, and their expression is correlated with hormone receptor expression, htRNAs could be used as biomarkers for diagnosis and prognosis of breast and prostate cancers. Also, htRNAs could be targets for novel therapeutic applications.

Methods for Quantifying a 5'-htRNA

In various embodiments, the present invention provides a method for quantifying a 5'-htRNA in an RNA sample. In some embodiments, the method includes (a) treating the RNA sample with a polynucleotide kinase; (b) adding a 3'-RNA adaptor to the RNA sample; (c) treating the RNA sample with an RNA ligase; (d) adding an oligonucleotide probe targeting the boundary between the 5'-htRNA and the 3'-RNA adaptor to the RNA sample; (e) performing a quantitative RT-PCR (qRT-PCR) on the RNA sample; and (0 quantifying the 5'-htRNA in the RNA sample by detecting the qRT-PCR product. In some embodiments, the invention provides a nucleic acid generated according to this method.

In further embodiments, the present invention provides a kit. In certain embodiments, the kit includes a polynucleotide kinase; a 3'-RNA adaptor; an RNA ligase; an oligonucleotide probe targeting the boundary between a 5'-htRNA and the 3'-RNA adaptor; and instructions for using the kit to quantify the 5'-htRNA in a sample.

In various embodiments described herein, the 5'-htRNA is 5'-htRNA$^{Asp}$ or 5'-htRNA$^{His}$.

In various embodiments, the RNA sample is total RNA. In certain embodiments, the RNA sample is derived from a cell, tissue, or organ. In some embodiments, the RNA sample is derived from a cancerous cell, tissue, or organ. In certain embodiments, the RNA sample is approximately at least 1 ng. In certain embodiments, the RNA sample is approximately 1-100 or 100-1000 ng. In certain embodiments, the RNA sample is approximately at least 100 pg.

In various embodiments, the polynucleotide kinase is a T4 polynucleotide kinase. In various embodiments, the RNA ligase is a T4 RNA ligase. In various embodiments, the oligonucleotide probe is a TaqMan probe. One of skill in the art would readily appreciate that kinases, ligases and probes with similar functions as those specifically listed are contemplated within the invention.

Methods for Quantifying a 3'-htRNA

In various embodiments, the present invention provides a method for quantifying a 3'-htRNA in an RNA sample. In certain embodiments, the method includes (a) treating the RNA sample with a polynucleotide kinase; (b) adding a 5'-RNA adaptor to the RNA sample; (c) treating the RNA sample with an RNA ligase; (d) adding an oligonucleotide probe targeting the boundary between the 5'-RNA adaptor and the 3'-htRNA to the RNA sample; (e) performing a quantitative RT-PCR (qRT-PCR) on the RNA sample; and (0 quantifying the 3'htRNA in the RNA sample by detecting the qRT-PCR product. In some embodiments, the method provides a nucleic acid generated according to this method.

In certain embodiments, the present invention provides a kit. In some embodiments, the kit includes a polynucleotide kinase; a 5'-RNA adaptor; an RNA ligase; an oligonucleotide probe targeting the boundary between the 5'-RNA adaptor and a 3'-htRNA; and instructions for using the kit to quantify the 3'-htRNA in a sample.

In certain embodiments, the 3'-htRNA is 3'-htRNA$^{Asp}$.

In various embodiments, the RNA sample is total RNA. In some embodiments, the RNA sample is derived from a cell, tissue, or organ. In certain embodiments, the RNA sample is derived from a cancerous cell, tissue, or organ. In certain embodiments, the RNA sample is approximately at least 1 ng. In certain embodiments, the RNA sample is approximately 1-100 or 100-1000 ng. In certain embodiments, the RNA sample is approximately at least 100 pg.

In various embodiments, the polynucleotide kinase is a T4 polynucleotide kinase. In various embodiments, the RNA ligase is a T4 RNA ligase. In various embodiments, the oligonucleotide probe is a TaqMan probe. One of skill in the art would readily appreciate that kinases, ligases and probes with similar functions as those specifically listed are contemplated within the invention.

Methods for Obtaining a DNA Library of 5'-htRNAs

Various embodiments of the present invention provide a method for obtaining a DNA library of 5'-htRNAs in an RNA sample. In some embodiments, the method includes (a) deacylating the RNA sample with a buffer having a pH value of at least 9.0; (b) treating the RNA sample with an alkaline phosphatase; (c) disrupting a 3'-OH end in the RNA sample with NaIO$_4$ oxidation; (d) treating the RNA sample with a polynucleotide kinase; (e) adding a 3'-RNA adaptor to the RNA sample; (f) treating the RNA sample with an RNA ligase; (g) adding a 5'-RNA adaptor to the RNA sample; (h) treating the RNA sample with an RNA ligase; and (i) performing a RT-PCR on the RNA sample, thereby obtaining the DNA library of 5'-htRNAs in the RNA sample. In some embodiments, the method provides a DNA library of 5'-htRNAs obtained by this method.

In various embodiments, the method further includes enriching one or more 25-55 nt RNA fragments in the RNA sample prior to step (a). In some embodiments, the method further includes gel-purifying one or more 25-55 nt RNA fragments in the RNA sample prior to step (a). In additional embodiments, the method further includes sequencing the DNA library of 5'-htRNAs in the RNA sample.

Methods for Obtaining a DNA Library of 3'-htRNAs

Various embodiments of the present invention provide a method for obtaining a DNA library of 3'-htRNAs in an RNA sample. In some embodiments, the method includes (a) treating the RNA sample with a polynucleotide kinase; (b) disrupting 3'-OH ends in the RNA sample with NaIO$_4$ oxidation; (c) deacylating the RNA sample with a buffer having a pH value of at least 9.0; (d) adding a 3'-RNA adaptor to the RNA sample; (e) treating the RNA sample with an RNA ligase; (f) adding a 5'-RNA adaptor to the RNA sample; (g) treating the RNA sample with an RNA ligase; and (h) performing a RT-PCR on the RNA sample, thereby obtaining the DNA library of 3'-htRNAs in the RNA sample. In some embodiments, the invention also provides a DNA library of 3'-htRNAs obtained by this method.

In some embodiments, the method further includes enriching one or more 25-55 nt RNA fragments in the RNA sample prior to step (a). In some embodiments, the method further includes gel-purifying one or more 25-55 nt RNA fragments in the RNA sample prior to step (a). In certain embodiments, the method further includes sequencing the DNA library of 3'-htRNAs in the RNA sample.

Methods for Determining the Presence or Absence of a Cancer Cell

Various embodiments of the present invention provide a method for determining the presence or absence of a cancer cell in a biological sample. In some embodiments, the method includes (a) obtaining an RNA sample from the biological sample; (b) quantifying an htRNA in the RNA sample; and (c) determining the presence of a cancer cell in the biological sample if the quantified htRNA is more than a reference value of the htRNA quantity, or determining the absence of a cancer cell in the biological sample if the quantified htRNA is not more than a reference value of the htRNA quantity. In various embodiments, the cancer cell is a prostate cancer cell or a breast cancer cell. In various embodiments, the cancer cell is a luminal-type breast cancer cell.

In some embodiments, the biological sample is a cell, tissue, organ, blood, serum, urine, saliva, lymph, plasma, semen, or a combination thereof.

In various embodiments, the htRNA referenced in this section is 5'-htRNA or 3'-htRNA. In various embodiments, the htRNA referenced in this section is 5'-htRNA$^{Asp}$, 5'-htRNA$^{His}$, or 3'-htRNA$^{Asp}$.

In some embodiments, the htRNA in the RNA sample is quantified according to a method described herein for quantifying a 5'-htRNA. In other embodiments, the htRNA in the RNA sample is quantified according to a method described herein for quantifying a 3'-htRNA.

Methods of Diagnosing and/or Prognosing Cancer

Various embodiments of the present invention provide a method of diagnosing cancer in a subject. In some embodiments, the method includes (a) obtaining a biological sample from the subject; (b) obtaining an RNA sample from the biological sample; (c) quantifying an htRNA in the RNA sample; and (d) diagnosing that the subject has cancer if the quantified htRNA is more than a reference value of the htRNA quantity, or diagnosing that the subject does not have cancer if the quantified htRNA is not more than a reference value of the htRNA quantity.

Various embodiments of the present invention provide a method of prognosing cancer in a subject. In some embodiments, the method includes (a) obtaining a biological sample from the subject; (b) obtaining an RNA sample from the biological sample; (c) quantifying an htRNA in the RNA sample; and (d) prognosing that the subject is likely to develop cancer if the quantified htRNA is more than a reference value of the htRNA quantity, or prognosing that the subject is not likely to develop cancer if the quantified htRNA is not more than a reference value of the htRNA quantity.

In various embodiments, the cancer detected, diagnosed, or prognosed using the inventive methods is prostate cancer or breast cancer. In various embodiments, the cancer is luminal-type breast cancer. In some embodiments, the subject is a human. In some embodiments, the subject is a mammal. In certain embodiments, the subject is a monkey, ape, dog, cat, cow, horse, goat, pig, rabbit, mouse or rat.

In various embodiments, the biological sample is a cell, tissue, organ, blood, serum, urine, saliva, lymph, plasma, semen, or a combination thereof.

In various embodiments, the htRNA described in this section is 5'-htRNA or 3'-htRNA. In various embodiments, the htRNA is 5'-htRNA$^{Asp}$, 5'-htRNA$^{His}$, or 3'-htRNA$^{Asp}$.

In other embodiments, the htRNA in the RNA sample is quantified according to a method described herein for quantifying a 5'-htRNA. In some embodiments, the htRNA in the RNA sample is quantified according to a method described herein for quantifying a 3'-htRNA.

Reference Values of htRNA

In various embodiments, the reference value of an htRNA quantity is the median or mean value of the htRNA quantity in a biological sample having no cancer cell. In various embodiments, the reference value of an htRNA quantity is the median or mean value of the htRNA quantity in a biological sample having no prostate cancer cell or breast cancer cell. In various embodiments, the reference value of an htRNA quantity is the median or mean value of the htRNA quantity in a biological sample having no luminal-type breast cancer cell. In accordance with the present invention, the number of biological samples used to compute a reference value can be at least 1, 2, 5, 10, 20, 30, 40, 50, 100, or 200.

In various embodiments, the reference value of an htRNA quantity is the median or mean value of the htRNA quantity in a non-cancerous cell, tissue or organ. In various embodiments, the reference value of an htRNA quantity is the median or mean value of the htRNA quantity in a non-breast and non-prostate cancer cell. In accordance with the present invention, the number of cells, tissues or organs used to compute a reference value can be at least 1, 2, 5, 10, 20, 30, 40, 50, 100, or 200.

In various embodiments, the reference value of an htRNA quantity is the median or mean value of the htRNA quantity in biological samples from a population of subjects having no cancer. In various embodiments, the reference value of an htRNA quantity is the median or mean value of the htRNA quantity in biological samples from a population of subjects having no prostate cancer or breast cancer. In various embodiments, the reference value of an htRNA quantity is the median or mean value of the htRNA quantity in biological samples from a population of subjects having no luminal-type breast cancer. In accordance with the present invention, the number of biological samples or subjects used to compute a reference value can be at least 1, 2, 5, 10, 20, 30, 40, 50, 100, or 200.

In additional embodiments, the reference value of an htRNA quantity is the htRNA quantity in a biological sample obtained from the subject at a different (for example, an earlier or later) time point, such as during diagnosis, after diagnosis, before treatment, during treatment, after treatment, or a combination thereof.

Various statistical methods, for example, a two-tailed student t-test with unequal variation, may be used to measure the difference between an htRNA quantity in a biological sample and a reference value of an htRNA quantity. Various statistical methods, for example, a two-tailed student t-test with unequal variation, may be used to measure the differences in quantities of an htRNA between a biological sample and a control sample from a normal/healthy individual, a subject having no cancer, a subject having no prostate cancer or breast cancer, or a subject having no luminal-type breast cancer. A significant difference may be determined where the p value is equal to or less than 0.05.

In various embodiments, an htRNA is determined to be more than a reference value of an htRNA quantity by at least or about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 400, 500, 600, 700, 900, or 1000%. In various embodiments, an htRNA is quantified to be more than a reference value of the htRNA quantity by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 4-fold, 5-fold, 6-fold, 7-fold, 8-fold, 9-fold or 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold.

The present invention may be as defined in any one of the following numbered paragraphs.

1. A method for quantifying a 5'-htRNA in an RNA sample, comprising:
   (a) treating the RNA sample with a polynucleotide kinase;
   (b) adding a 3'-RNA adaptor to the RNA sample;
   (c) treating the RNA sample with an RNA ligase;

(d) adding an oligonucleotide probe targeting the boundary between the 5'-htRNA and the 3'-RNA adaptor to the RNA sample;
(e) performing a quantitative RT-PCR (qRT-PCR) on the RNA sample; and
(f) quantifying the 5'-htRNA in the RNA sample by detecting the qRT-PCR product.

2. The method of paragraph 1, wherein the 5'-htRNA is 5'-htRNA$^{Asp}$ or 5'-htRNA$^{His}$.

3. The method of paragraph 1 or 2, wherein the RNA sample is total RNA.

4. The method of paragraph 1, 2, or 3, wherein the RNA sample is derived from a cell, tissue, or organ.

5. The method of any one of paragraphs 1-4, wherein the RNA sample is derived from a cancerous cell, tissue, or organ.

6. The method of any one of paragraphs 1-5, wherein the RNA sample is approximately at least 100 pg.

7. The method of any one of paragraphs 1-6, wherein the polynucleotide kinase is a T4 polynucleotide kinase.

8. The method of any one of paragraphs 1-7, wherein the RNA ligase is a T4 RNA ligase.

9. The method of any one of paragraphs 1-8, wherein the oligonucleotide probe is a TaqMan probe.

10. A nucleic acid generated according to the method of any one of paragraphs 1-9.

11. A kit, comprising:
(a) a polynucleotide kinase;
(b) a 3'-RNA adaptor;
(c) an RNA ligase;
(d) an oligonucleotide probe targeting the boundary between a 5'-htRNA and the 3'-RNA adaptor; and
(e) instructions for using the kit to quantify the 5'-htRNA in a sample.

12. A method for quantifying a 3'-htRNA in an RNA sample, comprising:
(a) treating the RNA sample with a polynucleotide kinase;
(b) adding a 5'-RNA adaptor to the RNA sample;
(c) treating the RNA sample with an RNA ligase;
(d) adding an oligonucleotide probe targeting the boundary between the 5'-RNA adaptor and the 3'-htRNA to the RNA sample;
(e) performing a quantitative RT-PCR (qRT-PCR) on the RNA sample; and
(f) quantifying the 3'htRNA in the RNA sample by detecting the qRT-PCR product.

13. The method of paragraph 12, wherein the 3'-htRNA is 3'-htRNA$^{Asp}$.

14. The method of paragraph 12 or 13, wherein the RNA sample is total RNA.

15. The method of paragraph 12, 13, or 14, wherein the RNA sample is derived from a cell, tissue, or organ.

16. The method of any one of paragraphs 12-15, wherein the RNA sample is derived from a cancerous cell, tissue, or organ.

17. The method of any one of paragraphs 12-16, wherein the RNA sample is approximately at least 100 pg.

18. The method of any one of paragraphs 12-17, wherein the polynucleotide kinase is a T4 polynucleotide kinase.

19. The method of any one of paragraphs 12-18, wherein the RNA ligase is a T4 RNA ligase.

20. The method of any one of paragraphs 12-19, wherein the oligonucleotide probe is a TaqMan probe.

21. A nucleic acid generated according to the method of any one of paragraphs 12-20.

22. A kit, comprising:
(a) a polynucleotide kinase;
(b) a 5'-RNA adaptor;
(c) an RNA ligase;
(d) an oligonucleotide probe targeting the boundary between the 5'-RNA adaptor and a 3'-htRNA; and
(e) instructions for using the kit to quantify the 3'-htRNA in a sample.

23. A method for obtaining a DNA library of 5'-htRNAs in an RNA sample, comprising:
(a) deacylating the RNA sample with a buffer having a pH value of at least 9.0;
(b) treating the RNA sample with an alkaline phosphatase;
(c) disrupting a 3'-OH end in the RNA sample with NaIO$_4$ oxidation;
(d) treating the RNA sample with a polynucleotide kinase;
(e) adding a 3'-RNA adaptor to the RNA sample;
(f) treating the RNA sample with an RNA ligase;
(g) adding a 5'-RNA adaptor to the RNA sample;
(h) treating the RNA sample with an RNA ligase; and
(i) performing a RT-PCR on the RNA sample, thereby obtaining the DNA library of 5'-htRNAs in the RNA sample.

24. The method of paragraph 23, further comprising enriching one or more 25-55 nt RNA fragments in the RNA sample prior to step (a).

25. The method of paragraph 23 or 24, further comprising gel-purifying one or more 25-55 nt RNA fragments in the RNA sample prior to step (a).

26. The method of paragraph 23, 24, or 25, further comprising sequencing the DNA library of 5'-htRNAs in the RNA sample.

27. A DNA library of 5'-htRNAs obtained by the method of any one of paragraphs 23-26.

28. A method for obtaining a DNA library of 3'-htRNAs in an RNA sample, comprising:
(a) treating the RNA sample with a polynucleotide kinase;
(b) disrupting 3'-OH ends in the RNA sample with NaIO$_4$ oxidation;
(c) deacylating the RNA sample with a buffer having a pH value of at least 9.0;
(d) adding a 3'-RNA adaptor to the RNA sample;
(e) treating the RNA sample with an RNA ligase;
(f) adding a 5'-RNA adaptor to the RNA sample;
(g) treating the RNA sample with an RNA ligase; and
(h) performing a RT-PCR on the RNA sample, thereby obtaining the DNA library of 3'-htRNAs in the RNA sample.

29. The method of paragraph 28, further comprising enriching one or more 25-55 nt RNA fragments in the RNA sample prior to step (a).

30. The method of paragraph 28 or 29, further comprising gel-purifying one or more 25-55 nt RNA fragments in the RNA sample prior to step (a).

31. The method of paragraph 28, 29, or 30, further comprising sequencing the DNA library of 3'-htRNAs in the RNA sample.

32. A DNA library of 3'-htRNAs obtained by the method of any one of paragraphs 28-31.

33. A method for determining the presence or absence of a cancer cell in a biological sample, comprising:
(a) obtaining an RNA sample from the biological sample;
(b) quantifying an htRNA in the RNA sample; and
(c) determining the presence of a cancer cell in the biological sample if the quantified htRNA is more than a reference value of the htRNA quantity, or determining the absence of a cancer cell in the biological sample if the quantified htRNA is not more than a reference value of the htRNA quantity.

34. The method of paragraph 33, wherein the cancer cell is a prostate cancer cell or a breast cancer cell.

35. The method of paragraph 33 or 34, wherein the cancer cell is a luminal-type breast cancer cell.

36. The method of paragraph 33, 34, or 35, wherein the biological sample is a cell, tissue, organ, blood, serum, urine, saliva, lymph, plasma, semen, or a combination thereof.

37. The method of any one of paragraphs 33-36, wherein the htRNA is 5'-htRNA or 3'-htRNA.

38. The method of any one of paragraphs 33-37, wherein the htRNA is 5'-htRNA$^{Asp}$, 5'-htRNA$^{His}$, or 3'-htRNA$^{Asp}$.

39. The method of any one of paragraphs 33-38, wherein the htRNA in the RNA sample is quantified according to the method of paragraph 1.

40. The method of any one of paragraphs 33-39, wherein the htRNA in the RNA sample is quantified according to the method of any one of paragraphs 12-15.

41. A method of diagnosing cancer in a subject, comprising:
(a) obtaining a biological sample from the subject;
(b) obtaining an RNA sample from the biological sample;
(c) quantifying an htRNA in the RNA sample; and
(d) diagnosing that the subject has cancer if the quantified htRNA is more than a reference value of the htRNA quantity, or diagnosing that the subject does not have cancer if the quantified htRNA is not more than a reference value of the htRNA quantity.

42. A method of prognosing cancer in a subject, comprising:
(a) obtaining a biological sample from the subject;
(b) obtaining an RNA sample from the biological sample;
(c) quantifying an htRNA in the RNA sample; and
(d) prognosing that the subject is likely to develop cancer if the quantified htRNA is more than a reference value of the htRNA quantity, or prognosing that the subject is not likely to develop cancer if the quantified htRNA is not more than a reference value of the htRNA quantity.

43. The method of paragraph 41 or 42, wherein the cancer is prostate cancer or breast cancer.

44. The method of paragraph 41, 42, or 43, wherein the cancer is luminal-type breast cancer.

45. The method of any one of paragraphs 41-44, wherein the subject is a human.

46. The method of any one of paragraphs 41-45, wherein the biological sample is a cell, tissue, organ, blood, serum, urine, saliva, lymph, plasma, semen, or a combination thereof.

47. The method of any one of paragraphs 41-46, wherein the htRNA is 5'-htRNA or 3'-htRNA.

48. The method of any one of paragraphs 41-47, wherein the htRNA is 5'-htRNA$^{Asp}$, 5'-htRNA$^{His}$, or 3'-htRNA$^{Asp}$.

49. The method of any one of paragraphs 41-48, wherein the htRNA in the RNA sample is quantified according to the method of paragraph 1.

50. The method of any one of paragraphs 41-49, wherein the htRNA in the RNA sample is quantified according to the method of paragraph 12.

51. The method of any one of paragraphs 33-50, wherein the reference value of the htRNA quantity is the median or mean value of the htRNA quantity in a biological sample having no cancer cell.

52. The method of any one of paragraphs 33-50, wherein the reference value of the htRNA quantity is the median or mean value of the htRNA quantity in a biological sample having no prostate cancer cell or breast cancer cell.

53. The method of any one of paragraphs 33-50, wherein the reference value of the htRNA quantity is the median or mean value of the htRNA quantity in a biological sample having no luminal-type breast cancer cell.

54. The method of any one of paragraphs 33-50, wherein the reference value of the htRNA quantity is the median or mean value of the htRNA quantity in a non-cancerous cell, tissue, or organ.

55. The method of any one of paragraphs 33-50, wherein the reference value of the htRNA quantity is the median or mean value of the htRNA quantity in a non-breast and non prostate cancer cell.

56. The method of any one of paragraphs 33-50, wherein the reference value of the htRNA quantity is the median or mean value of the htRNA quantity in biological samples from a population of subjects having no cancer.

57. The method of any one of paragraphs 33-50, wherein the reference value of the htRNA quantity is the median or mean value of the htRNA quantity in biological samples from a population of subjects having no prostate cancer or breast cancer.

58. The method of any one of paragraphs 33-50, wherein the reference value of the htRNA quantity is the median or mean value of the htRNA quantity in biological samples from a population of subjects having no luminal-type breast cancer.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Discovery of htRNAs

Figures 2A, 2B:
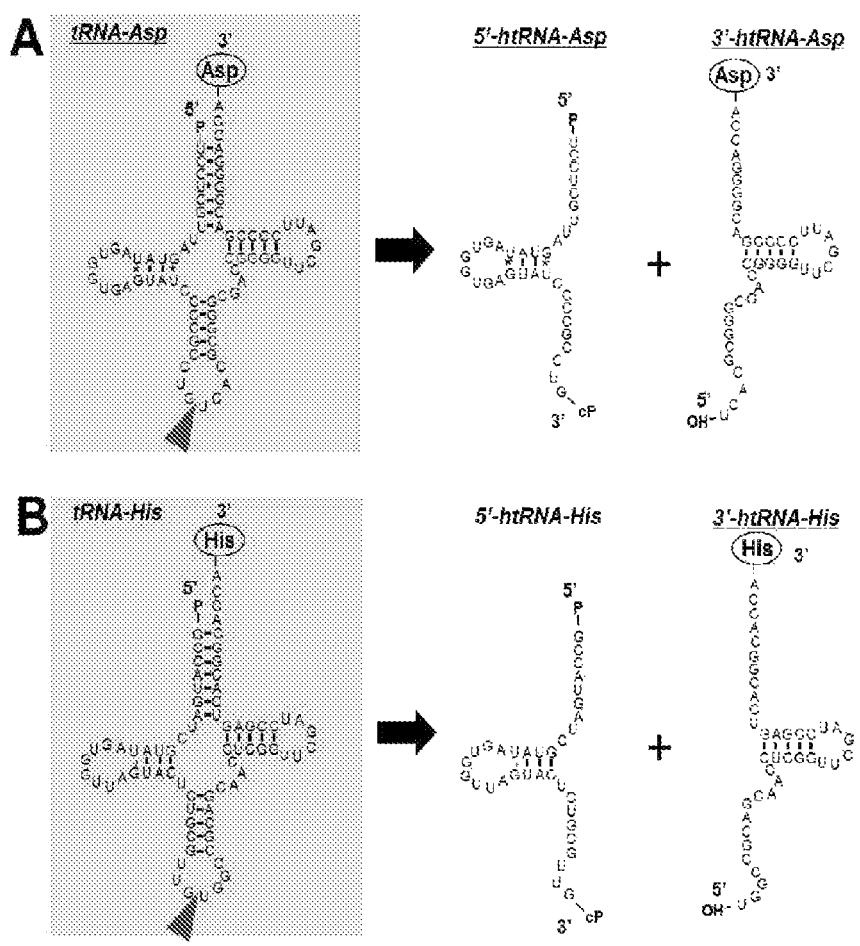
FIGS. 2A-2B demonstrate, in accordance with an embodiment of the invention, sequences of htRNAs derived from tRNA$^{Asp}$ and tRNA$^{His}$. The arrow heads indicate the border between 5'-htRNA$^{Asp}$ and 3'-htRNA$^{Asp}$ and the border between 5'-htRNA$^{His}$ and 3'-htRNA$^{His}$. Sequences of htRNA$^{Asp}$ (FIG. 2A) and htRNA$^{His}$ (FIG. 2B) were determined by RACE by using total RNA from BT474 breast cancer cells. Terminal structures of htRNAs were determined by a combination of NaIO$_4$ oxidation/β-elimination reaction, phosphatase and kinase treatments, and deacylation reactions as previously described in Kirino, Y. and Z. Mourelatos, Mouse Piwi-interacting RNAs are 2'-O-methylated at their 3' termini. *Nat Struct Mol Biol*, 2007. 14(4): p. 347-8), which is incorporated herein by reference in its entirety as though fully set forth. It was determined that 5'-htRNAs contain a mono-phosphate (P) at their 5'-end and a cyclic-phosphate (cP) at their 3'-end, whereas 3'-htRNAs contain a hydroxyl (OH) at their 5'-end and an amino acid at their 3'-end.

Gene expression during cancer development is controlled by a wide array of regulatory molecules, including small non-coding RNAs (sncRNAs), such as microRNAs. Certain embodiments of the present invention are based upon the discovery that htRNAs (a novel type of sncRNA derived from tRNAs) are expressed in breast and prostate cancers. htRNAs are 35-50 nucleotides (nt) long, and generated by angiogenin (ANG)-mediated cleavage at the anticodon of mature tRNAs (FIG. 1). Both 5'- (5'-htRNAs) and 3'-halves (3'-htRNAs) are derived from at least cytoplasmic tRNA$^{Asp}$ and tRNA$^{His}$ (FIG. 2). 5'-htRNAs contain a mono-phosphate at their 5'-end and a cyclic-phosphate at their 3'-end, whereas 3'-htRNAs contain a hydroxyl at their 5'-end and an amino acid at their 3'-end (FIG. 2).

As described herein, a sensitive system for detecting htRNA expression was established, and htRNAs were determined to be expressed in relatively high levels in breast cancer and prostate cancer cells, and not in other cancer cells and non-cancerous cells tested. Moreover, htRNA abundance was associated with cell proliferation and hormone-receptor expression.

These results implicate htRNAs as novel, important factors in breast and prostate cancer pathogenesis and suggest the use of htRNAs as novel biomarkers for the two cancers.

Establishment of htRNA Detection System

Figure 4A:
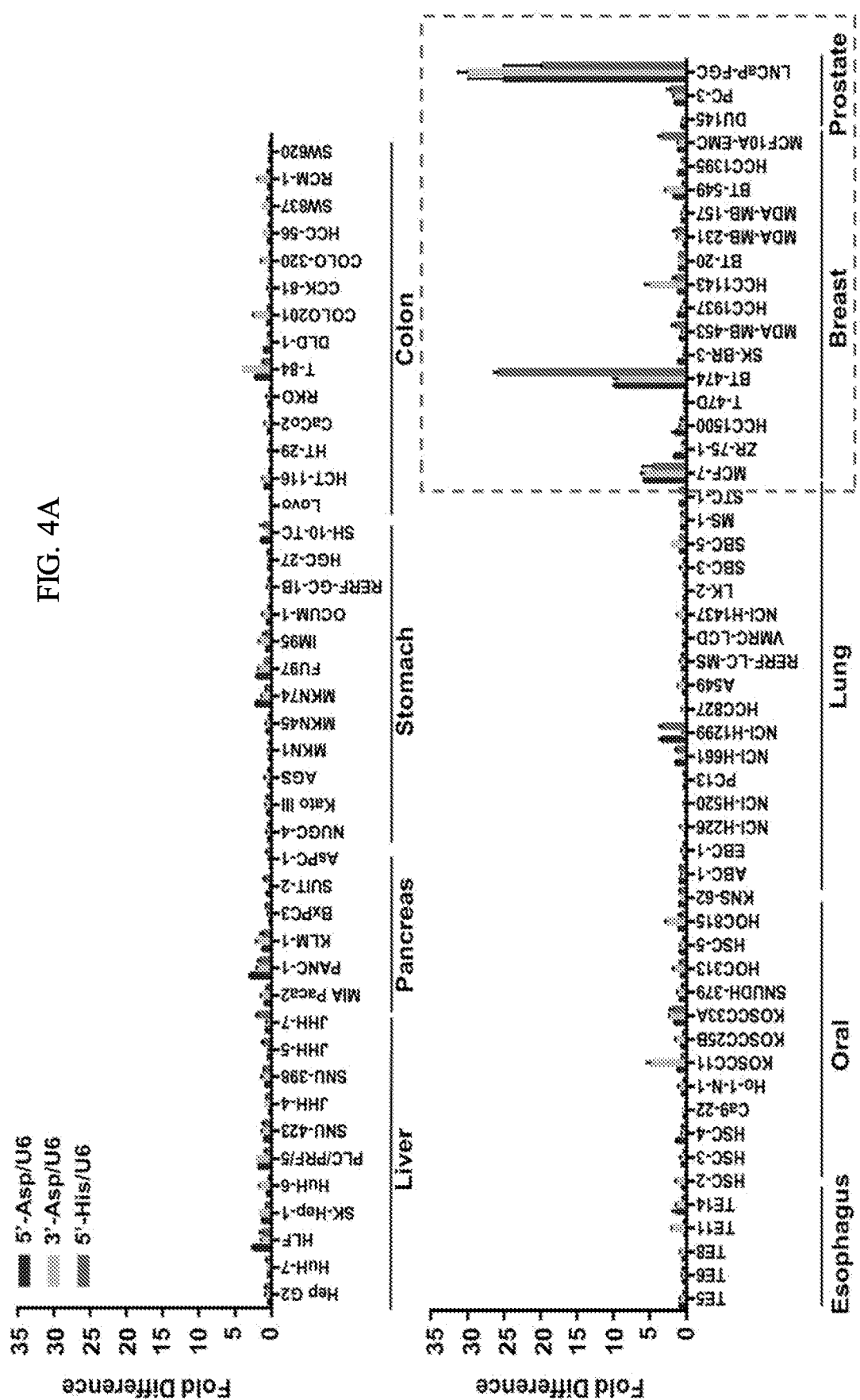
FIGS. 4A-4B demonstrate, in accordance with an embodiment of the invention, htRNA expression screening. Screenings were performed for 5'-htRNA$^{Asp}$, 3'-htRNA$^{Asp}$ and 5'-htRNA$^{His}$ expressions in 96 cancer cell lines. htRNA abundance in BT20 breast cancer cells was set as 1. The boxed portion of FIG. 4A is shown in FIG. 4B.
Figure 4B:
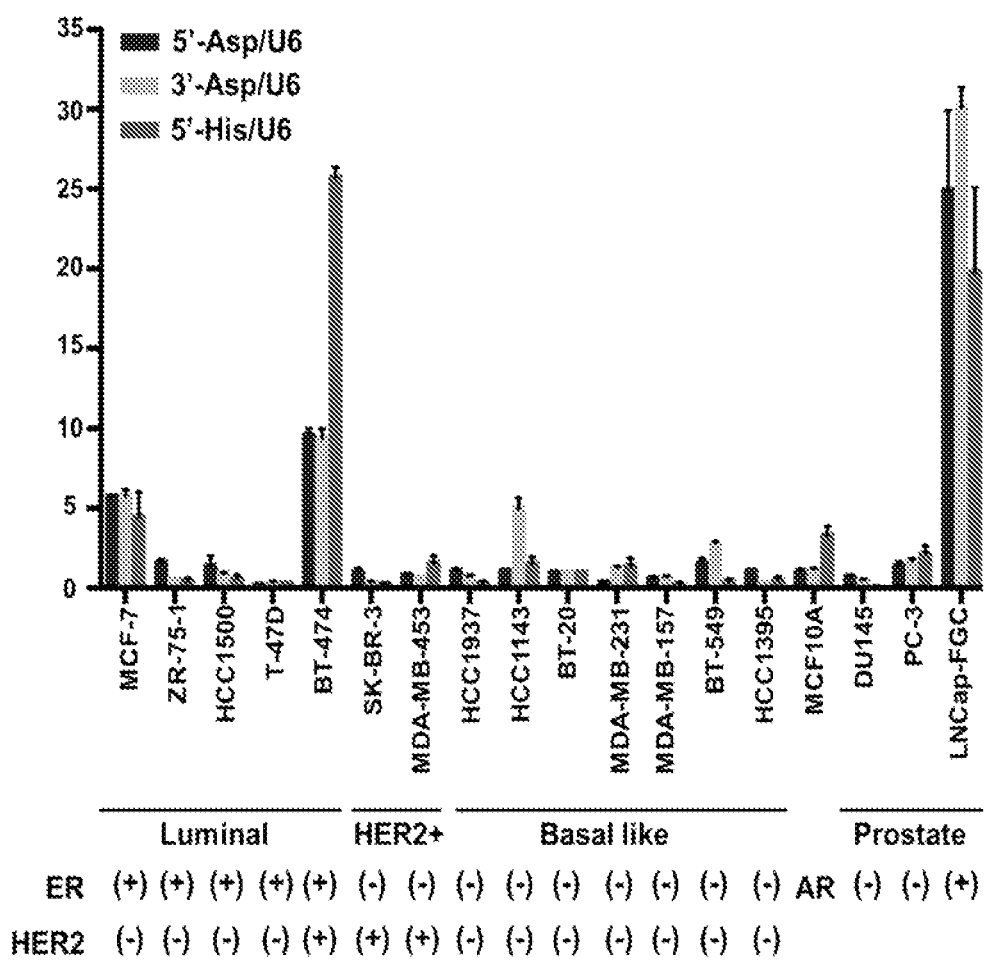

To widely screen for htRNA expression, a sensitive Taq-Man qRT-PCR-based method that detects htRNAs from about 100 pg of total RNA was established. For 5'-htRNA detection (FIG. 3A), total RNA was treated with T4 PNK to remove a cyclic phosphate at the 3'-end of 5'-htRNA, and subjected to 3'-RNA adapter ligation by T4 RNA Ligase. 5'-htRNA was then detected using qRT-PCR with a Taq-Man probe targeting the boundary between the htRNA and adapter. The inability to detect 5'-htRNA without T4 PNK or T4 RNA ligase indicated high specificity of this method. For 3'-htRNA detection (FIG. 3B), total RNA was treated with T4 PNK to add a phosphate at the 5'-end of 3'-htRNA, and subjected to 5'-RNA adapter ligation by T4 RNA Ligase. 3'-htRNA was then detected using qRT-PCR with a Taq-Man probe targeting the boundary between the htRNA and adapter. The low efficiency to detect 3'-htRNA without T4 PNK or T4 RNA ligase indicated high specificity of this method.

htRNAs are Abundantly and Specifically Expressed in Luminal-Type Breast Cancer and Prostate Cancer By using the detection system described herein, htRNA expression was measured in 96 cancer cell lines, revealing that htRNAs are abundantly and specifically present in luminal-type breast cancer and prostate cancer, but not in basal-like type breast cancer or other cancers (FIGS. 4A and 4B). These results suggest a relationship between hormone receptor expression and htRNA expression.

Figures 5A, 5B:
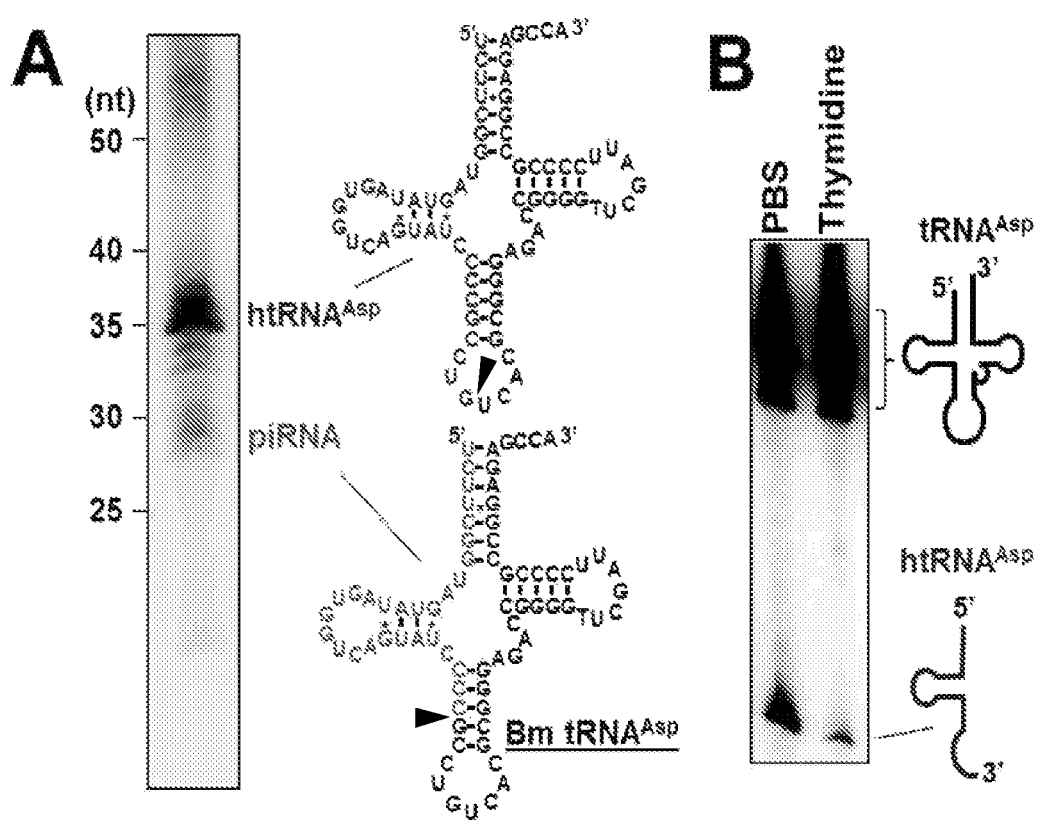
FIGS. 5A-5B demonstrate, in accordance with an embodiment of the invention, discovery of htRNAs in BmN4 cells.

Discovery of htRNA Expression that is Associated with Cell Proliferation in BmN4 Cells The biogenesis of piRNAs, a germline-specific class of small RNA, was investigated by taking advantage of *Bombyx mori*-derived BmN4 cells, as described in Honda, S., Mitochondrial protein BmPAPI modulates the length of mature piRNAs RNA, 2013. 19(10): p. 1405-18, which is incorporated herein by reference in its entirety as though fully set forth. During the analysis of a tRNA-derived piRNA, htRNAs derived from cytoplasmic tRNA$^{Asp}$ (FIG. 5A) and tRNA$^{His}$ (not shown) were detected. The correlation between htRNA expression and cell proliferation (FIG. 5B) suggests the expression and function of these molecules in cancer cells.

htRNA$^{Asp}$ and htRNA$^{His}$ are Expressed in Breast Cancer Cells

Figures 6A, 6B, 6C:
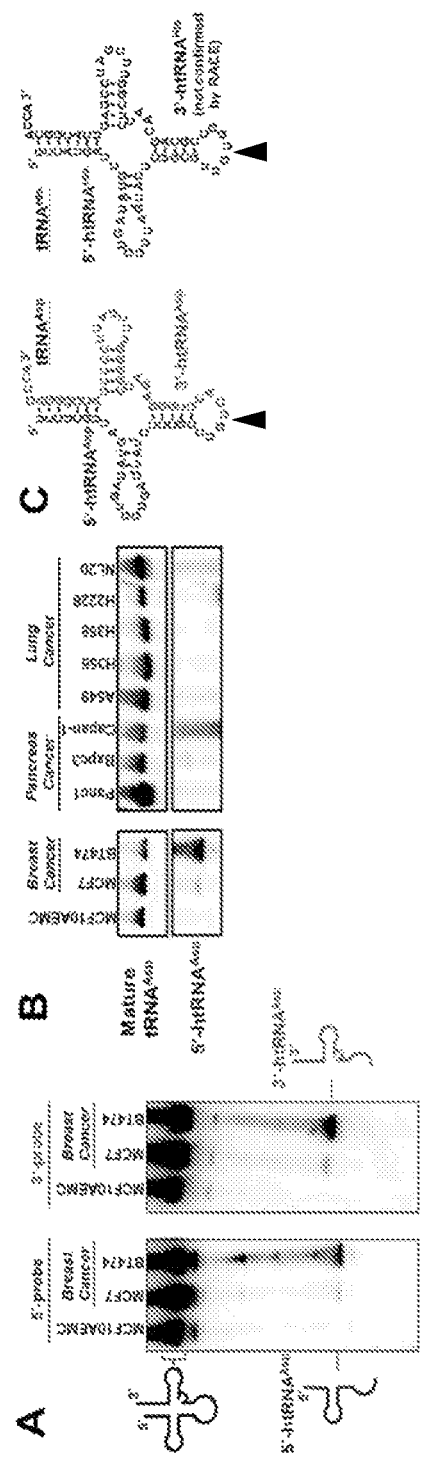
FIGS. 6A-6C demonstrate, in accordance with an embodiment of the invention, htRNA expression in breast cancer.

Interestingly, Northern blots revealed that both 5'- and 3'-htRNAs derived from tRNA$^{Asp}$ and tRNA$^{His}$ are present in MCF7 and BT474 human breast cancer cells at relatively high levels, but not in pancreas and lung cancer cells or in non-cancerous cells (FIGS. 6A and 6B). RACE showed that 5'-htRNA does not contain overlapping or intercalating sequences with 3'-htRNA (FIG. 6C), suggesting htRNA production from a single endonucleolytic cleavage. htRNAs derived from tRNA$^{Ser}$ or tRNA$^{Gly}$ were not detected, suggesting tRNA-specific htRNA production.

Figures 7A, 7B:
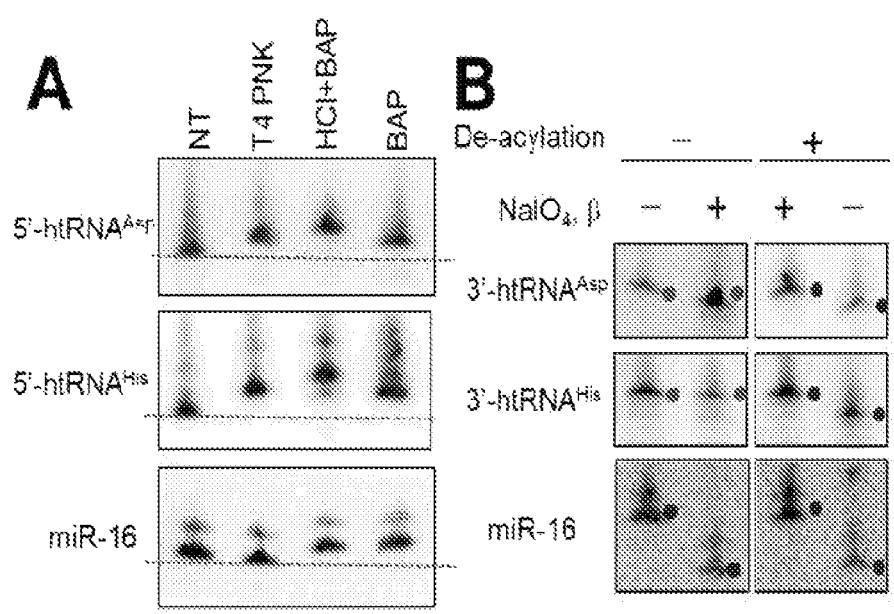
FIGS. 7A-7B demonstrate, in accordance with an embodiment of the invention, terminal structure analyses of htRNAs.

5'-htRNAs and 3'-htRNAs Contain Cyclic Phosphates and Amino Acids at their 3'-Termini, Respectively The terminal structures of htRNAs were determined using a combination of NaIO$_4$ oxidation/β-elimination reaction, phosphatase and kinase treatments, and deacylation reactions as previously described in Kirino, Y. and Z. Mourelatos, Mouse Piwi-interacting RNAs are 2'-O-methylated at their 3' termini. Nat Struct Mol Biol, 2007. 14(4): p. 347-8, which is incorporated herein by reference in its entirety as though fully set forth. It was determined that 5'-htRNAs contain a mono-phosphate at their 5'-end and a cyclic-phosphate at their 3'-end, whereas 3'-htRNAs contain a hydroxyl at their 5'-end and an amino acid at their 3'-end (FIGS. 7A and 7B).

Identification of the Comprehensive htRNA Repertoire in Breast Cancer

Figure 8:
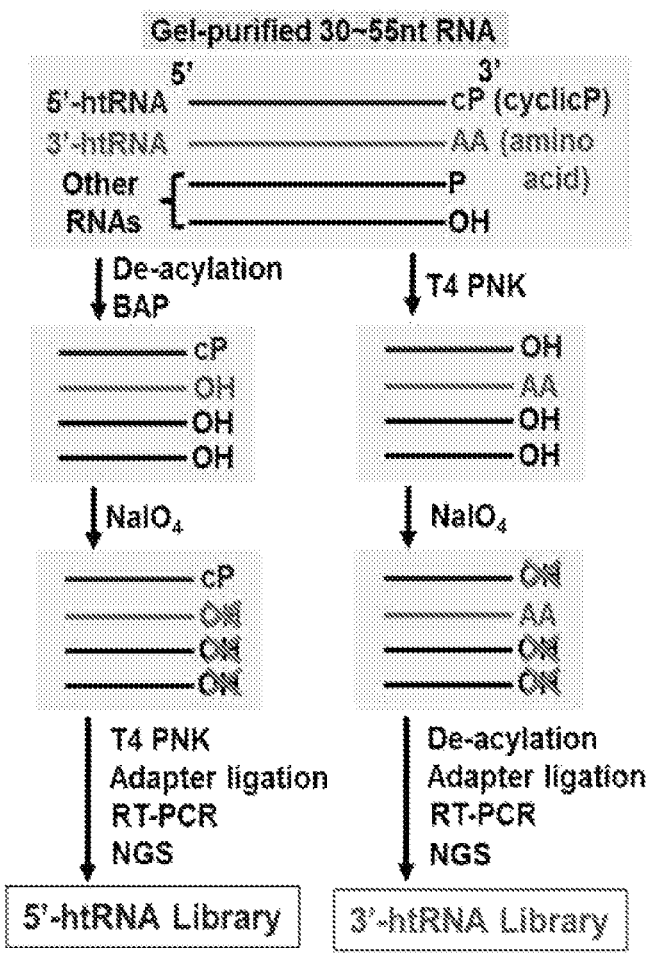
FIG. 8 demonstrates, in accordance with an embodiment of the invention, selective htRNA amplification and identification. Using total RNA from BT474 breast cancer cells, 30-55nt RNA fragments containing 5'-htRNAs with cyclic phosphate (cP), 3'-htRNAs with amino acid (AA), and other RNA species with either a phosphate (P) or a hydroxyl-terminus (OH) at their 3'-ends can be purified. To identify 5'-htRNAs, the purified RNA fraction can be deacylated and further treated with BAP, which removes AA and P, but not cP. Subsequent NaIO$_4$ oxidation disrupts the 3'-OH ends, and only those 5'-htRNAs with cP-blocked 3'-ends survive the treatment. These 5'-htRNAs are then treated with T4 PNK to remove cP and subsequently subjected to adapter ligations, RT-PCR and next-generation sequencing. To amplify 3'-htRNAs, the RNA fraction with T4 PNK is treated to remove P and cP, but not AA. In this case, only 3'-htRNAs, whose 3'-ends are blocked with AA, survive the subsequent NaIO$_4$ oxidation.

The first step towards understanding the biogenesis and precise molecular function of htRNAs in breast cancer will be to identify the complete htRNA repertoire. Utilizing the 3'-end characteristics of htRNAs, the specific species expressed in breast cancer will be selectively amplified and identified (FIG. 8). Detailed bioinformatics analyses of htRNA sequence reads will be used to confirm htRNA$^{Asp}$ and htRNA$^{His}$ expressions in addition to other htRNAs, and to identify the tRNA cleavage sites in htRNA biogenesis. The expression of the abundant htRNAs will be assessed in other cancer cells and patient tissues. In addition to BT474 cells, the htRNA repertoire in other htRNA-abundant breast cancer cells, such as MCF7, and in patient tissues will be further identified; the specificity, generality, and/or differences in the htRNA species and abundance will be investigated. These analyses will provide the first framework for the expression of htRNAs in cancer.

Figure 9:
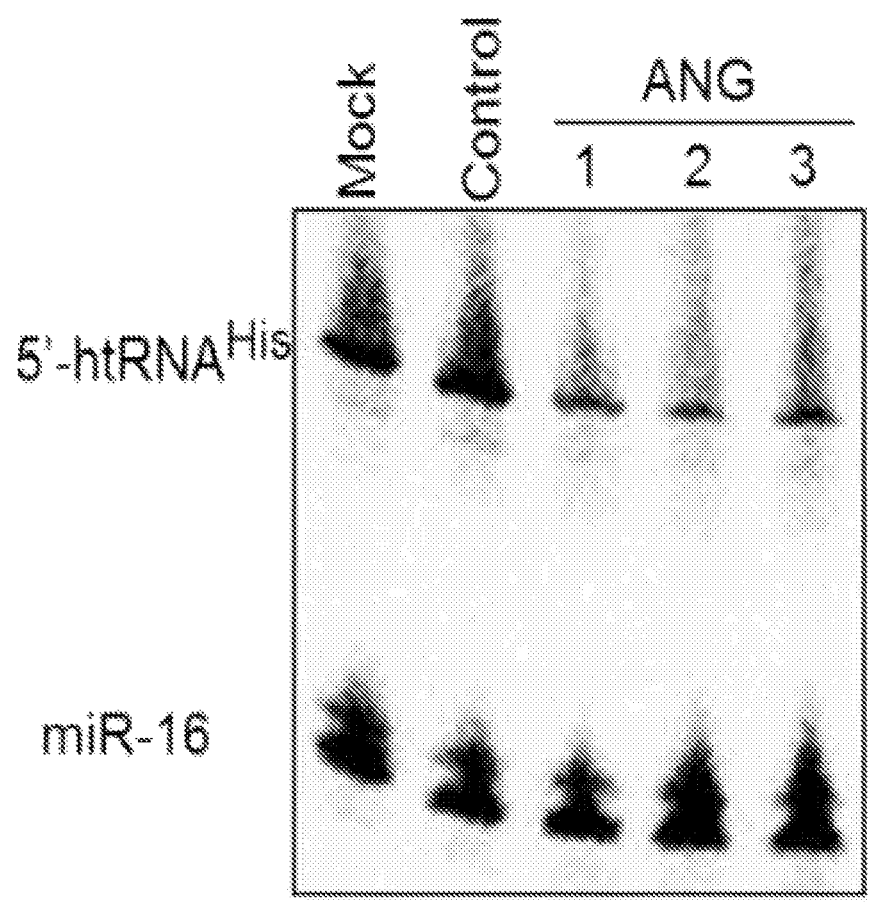
FIG. 9 demonstrates, in accordance with an embodiment of the invention, ANG mediates htRNA production. Northern blots were used to detect htRNA$^{His}$ in BT474 cells transfected with no siRNA (Mock), a control siRNA (Control), or three different siRNAs targeting ANG (ANG 1-3). The htRNA reduction induced by ANG depletion clearly indicates the involvement of ANG in htRNA production.

Understanding the Molecular Basis of Angiogenin-Mediated tRNA-Cleavage in htRNA Production The molecular mechanisms underlying htRNA biogenesis are unknown. In mammals, tiRNAs are produced by tRNA anticodon cleavage via the ANG ribonuclease (See Ivanov, P., et al., Angiogenin-induced tRNA fragments inhibit translation initiation. Mol Cell, 2011. 43(4): p. 613-23; Emara, M. M., et al., Angiogenin-induced tRNA-derived stress-induced RNAs promote stress-induced stress granule assembly. J Biol Chem, 2010. 285(14): p. 10959-68; Yamasaki, S., et al., Angiogenin cleaves tRNA and promotes stress-induced translational repression. J Cell Biol, 2009. 185(1): p. 35-42; and Fu, H., et al., Stress induces tRNA cleavage by angiogenin in mammalian cells. FEBS Lett, 2009. 583(2): p. 437-42). The research presented in the present application demonstrates that ANG is also responsible for htRNA production in breast cancer (FIG. 9). Recombinant human ANG protein could be produced and purified. In vitro reactions will be designed, in which the ANG protein is incubated with 32P-labeled in vitro-transcribed tRNA for anticodon cleavage. Using kinetic analyses of the various tRNA species and their mutants, the positive and negative determinants of tRNA sequences necessary for htRNA production will be determined to understand the molecular basis of ANG-mediated tRNA cleavage in breast cancer.

Understanding the Mechanisms Underlying the Specific Expression of the htRNAs in Breast Cancer htRNA expression is highly specific to breast cancer cells (FIG. 4A, FIG. 6B), and the precise molecular mechanisms behind this specificity will be investigated. While not wishing to be bound by a particular theory, some possible reasons that htRNAs are abundant in breast cancer could be (i) ANG is activated (Yamasaki, S., et al., Angiogenin cleaves tRNA and promotes stress-induced translational repression. J Cell Biol, 2009. 185(1): p. 35-42), or RNH1, an inhibitor of ANG, could be deactivated, and/or (ii) m5C methylation at position 38 of tRNA$^{Asp}$, which is mediated by DNMT2 and protects the tRNA from ANG-mediated anticodon cleavage, is deficient (See Goll, M. G., et al., Methylation of tRNAAsp by the DNA methyltransferase homolog Dnmt2. Science, 2006. 311(5759): p. 395-8; and Schaefer, M., et al., RNA methylation by Dnmt2 protects transfer RNAs against stress-induced cleavage. Genes Dev, 2010. 24(15): p. 1590-5). To address these hypotheses, the expression and localization of ANG, RNH1 and TRDMT1 in breast cancer cells and in other types of cancer cells will be analyzed. Furthermore, the rate of tRNAAsp-m5C38 modification in breast cancer cells will be investigated using biochemical analyses, including thin layer chromatography and the Donis-Keller method (See Kirino, Y. and Z. Mourelatos, Mouse Piwi-interacting RNAs are 2'-O-methylated at their 3' termini. *Nat Struct Mol Biol*, 2007. 14(4): p. 347-8, and Kirino, Y., et al., Codon-specific translational defect caused by a wobble modification deficiency in mutant tRNA from a human mitochondrial disease. *Proc Natl Acad Sci USA*, 2004. 101(42): p. 15070-5, which are each incorporated herein by reference in their entirety as though full set forth), and mass-spectrometry (See Kirino, Y., et al., Acquisition of the wobble modification in mitochondrial tRNALeu (CUN) bearing the G12300A mutation suppresses the MELAS molecular defect. *Hum Mol Genet*, 2006. 15(6): p. 897-904), which is incorporated herein by reference in its entirety as though full set forth).

htRNAs are Abundantly and Specifically Expressed in Luminal-Type Breast Cancer and Prostate Cancer To widely screen for htRNA expression, a sensitive Taq-Man qRT-PCR-based method that detects 5'-htRNAs from 100 pg of total RNA was established (FIG. 3A). htRNA expression was measured in 96 cancer cell lines, revealing that htRNAs are abundantly present in luminal-type breast cancer and prostate cancer (See comprehensive molecular portraits of human breast tumors. *Nature*, 2012. 490(7418): p. 61-70), but not in basal-like type breast cancer or other cancers.

Unraveling the Molecular Function of htRNAs in Luminal-Type Breast Cancer

The research described in this application strongly suggests an association between htRNA expression and the ER signaling pathways. The direct link will be explored by analyzing htRNA, ANG, RNH1 and DNMT2 expressions in BT474 cells with overexpressed or repressed ER and HER2. Without wishing to be bound by a particular theory, it is hypothesized that htRNAs are involved in gene expression regulation, as suggested by previous studies that described the roles for other tRNA-derived RNAs on the inhibitions of mRNA expression and translation (See Maute, R. L., et al., tRNA-derived microRNA modulates proliferation and the DNA damage response and is down-regulated in B cell lymphoma. *Proc Natl Acad Sci USA*, 2013. 110(4): p. 1404-9; Lee, Y. S., et al., A novel class of small RNAs: tRNA-derived RNA fragments (tRFs). *Genes Dev*, 2009. 23(22): p. 2639-49; and Ivanov, P., et al., Angiogenin-induced tRNA fragments inhibit translation initiation. *Mol Cell*, 2011. 43(4): p. 613-23, each of which is incorporated herein by reference as though fully set forth). htRNAs in BT474 cells could be silenced using 2'-O-methylated antisense oligonucleotides, and (1) global translation by pulse-labeling, (2) RNA expression by RNA-sequencing, and (3) the cell proliferation, colony formation, and migration rates will be investigated. These studies will help elucidate the precise biological function of htRNAs in breast and prostate cancers.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.)

What is claimed is:

1. A method for quantifying a 3'-htRNA in an RNA sample, comprising:
   (a) treating the RNA sample containing 3'-htRNAs having an amino acid with a polynucleotide kinase;
   (b) adding a 5'-RNA adaptor to the RNA sample;
   (c) treating the RNA sample with an RNA ligase;
   (d) adding an oligonucleotide probe targeting the boundary between the 5'-RNA adaptor and the 3'-htRNA to the RNA sample;
   (e) performing a quantitative RT-PCR (qRT-PCR) on the RNA sample; and
   (f) quantifying the 3'htRNA in the RNA sample by detecting the qRT-PCR product.

2. The method of claim 1, wherein the 3'-htRNA is 3'-htRNA$^{Asp}$.

3. The method of claim 1, wherein the RNA sample is total RNA.

4. The method of claim 1, wherein the RNA sample is derived from a cell, tissue, or organ; wherein the RNA sample is derived from a cancerous cell, tissue or organ, and is approximately at least 100 pg.

5. The method of claim 1, wherein the polynucleotide kinase is a T4 polynucleotide kinase; and wherein the RNA ligase is a T4 RNA ligase.

* * * * *

SEQUENCE LISTING

<160> NUMBER OF SEQ ID NOS: 8

<210> SEQ ID NO 1
<211> LENGTH: 74
<212> TYPE: RNA
<213> ORGANISM: Homo sapiens

<400> SEQUENCE: 1
uccucguuag uauaguggug aguauccccg ccugucacgc gggcgaccgg gguucgauuc     60
cccgacgggg acca                                                       74

<210> SEQ ID NO 2
<211> LENGTH: 34
<212> TYPE: RNA
<213> ORGANISM: Homo sapiens

<400> SEQUENCE: 2
uccucguuag uauaguggug aguauccccg ccug                                 34

<210> SEQ ID NO 3
<211> LENGTH: 40
<212> TYPE: RNA
<213> ORGANISM: Homo sapiens

<400> SEQUENCE: 3
ucacgcgggc gaccgggguu cgauuccccg acggggacca                           40

<210> SEQ ID NO 4
<211> LENGTH: 74
<212> TYPE: RNA
<213> ORGANISM: Homo sapiens

<400> SEQUENCE: 4
gccaugaucg uauagugguu aguacucugc guuguggccg cagcaaccuc gguucgaucc     60
gagucacggc acca                                                       74

```
<210> SEQ ID NO 5
<211> LENGTH: 34
<212> TYPE: RNA
<213> ORGANISM: Homo sapiens

<400> SEQUENCE: 5
gccaugaucg uauagugguu aguacucugc guug                                    34

<210> SEQ ID NO 6
<211> LENGTH: 40
<212> TYPE: RNA
<213> ORGANISM: Homo sapiens

<400> SEQUENCE: 6
uggccgcagc aaccucgguu cgauccgagu cacggcacca                              40

<210> SEQ ID NO 7
<211> LENGTH: 75
<212> TYPE: DNA
<213> ORGANISM: Homo sapiens
<220> FEATURE:
<223> OTHER INFORMATION: Description of Combined DNA/RNA Molecule: htRNA
      oligonucleotide

<400> SEQUENCE: 7
ucuucgguag uauagugguc aguauccccg ccugucacgc gggagaccgg ggtucgauuc         60
cccgccggag agcca                                                         75

<210> SEQ ID NO 8
<211> LENGTH: 75
<212> TYPE: RNA
<213> ORGANISM: Homo sapiens

<400> SEQUENCE: 8
uccucguuag uauaguggug aguauccccg ccugucacgc gggagaccgg gguucgauuc         60
cccgacgggg agcca                                                         75
```